United States Patent [19]

Guazzone et al.

[11] 4,397,953

[45] Aug. 9, 1983

[54] METHOD AND APPARATUS FOR ANAEROBIC FERMENTATION

[75] Inventors: Bruno Guazzone, Jona; Felix Müller, Stäfa, both of Switzerland

[73] Assignee: Process Engineering Company S A, Maennedorf, Switzerland

[21] Appl. No.: 235,134

[22] Filed: Feb. 17, 1981

[30] Foreign Application Priority Data

Feb. 26, 1980 [CH] Switzerland .......................... 1505/80

[51] Int. Cl.³ .......................... C12N 1/00; C12N 1/20; C12N 1/14; C12M 1/02
[52] U.S. Cl. .................................... 435/243; 435/253; 435/254; 435/262; 435/287; 435/316; 435/801
[58] Field of Search .............. 435/801, 316, 287, 313, 435/315, 262, 267, 41, 42, 243, 253, 254; 426/11, 15, 60

[56] References Cited

U.S. PATENT DOCUMENTS

| 3,308,037 | 3/1967 | Goos et al. | 435/316 X |
|---|---|---|---|
| 3,867,551 | 2/1975 | Jaegle | 426/11 |
| 4,001,090 | 1/1977 | Kalina | 435/316 X |
| 4,173,516 | 11/1979 | Katinger et al. | 435/286 |
| 4,283,497 | 8/1981 | Hirshaut | 435/316 X |
| 4,288,550 | 9/1981 | Ishida et al. | 435/801 X |
| 4,311,798 | 1/1982 | Katinger et al. | 435/313 X |

*Primary Examiner*—David M. Naff
*Attorney, Agent, or Firm*—Michael J. Striker

[57] ABSTRACT

Anaerobic fermentation of substrates with microorganisms is carried out by a process and with an apparatus wherein fermentation is conducted in a container having an upper cylindrical section, a lower conical section, and between the upper and lower sections an apertured bottom wall containing a plurality of openings. During fermentation, the substrate and microorganisms are recirculated from an outlet in the upper cylindrical section to an inlet in the lower conical section and upward in the container through the openings in the apertured bottom wall at sufficient fluid velocity to agitate the substrate and microorganisms therein and prevent settling of the microorganisms in the container. The apertured bottom wall serves as the sole means of agitation, and the use of this process and apparatus enables a significant reduction in the usual fermentation period.

12 Claims, 8 Drawing Figures

METHOD AND APPARATUS FOR ANAEROBIC FERMENTATION

BACKGROUND OF THE INVENTION

The invention concerns a method for submersed, anaerobic fermentation of substrates with microorganisms, as well as an apparatus for performance of the method.

Anaerobic fermentations are performed as a rule in agitator containers. The agitation is necessary so that the microorganisms do not deposit on the bottom of the container and thus become isolated from the content of substrate material which is supposed to be transformed. The agitation is also necessary to provide the microorganisms quickly enough with new untransformed substrate. Although the gaseous reaction products of the anaerobic fermentation do indeed on account of their buoyancy provide for a type of convection in the interior of the container, this is not ordinarily sufficient for a quick enough upheaval of substrate material. Owing to the slow movement of the substrate mass, fermentation times run more than 50 hours. Such fermentation times also do not work out to be less with use of the known energy-intensive mechanical stirring systems. In addition, with stirring mechanisms that lie in the interior of the container, there is an almost complete entry of kinetic energy into the substrate, which, in the form of heat, must be eliminated from the system.

Concerning this problem of eliminating the heat produced by mechanical stirring, a jet conveyor for a one-phase system in the form of a loop-reactor with interior revolution of the reactor contents has been suggested.

SUMMARY OF THE INVENTION

It is the object of the invention to drastically lower fermentation times by obtaining a revolution of substrate material with little introduction of heat.

This object is achieved according to the present invention through a method characterized in that for revolution of the substrate together with the microorganisms the substrate liquid itself serves as a sort of propellant, and its movement is promoted through openings in an apertured bottom attached between the lower conical part of the container and the cylindrical upper part of the container. The substrate material is recirculated from the upper part of the container. In addition, the invention encompasses an apparatus for accomplishing the method, characterized in that for increasing the substrate velocity within the container an apertured bottom is attached between the cylindrical part and the conical part.

The configuration of the openings in the apertured bottom and their distribution are significant.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
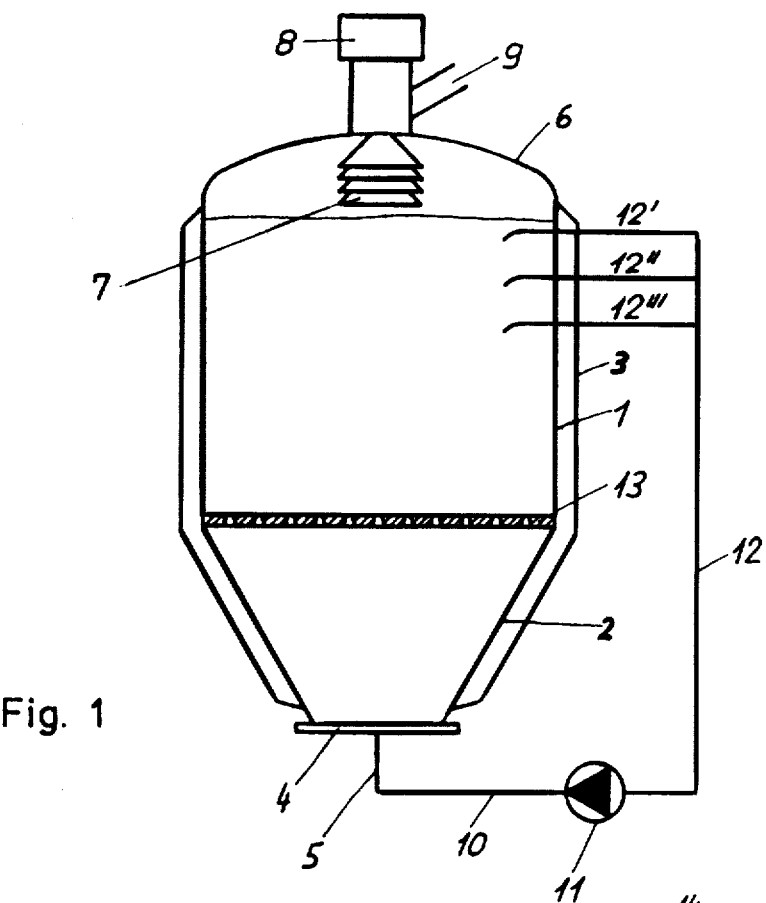
FIG. 1 is a fermentation container in vertical cross-section.
Figure 2:
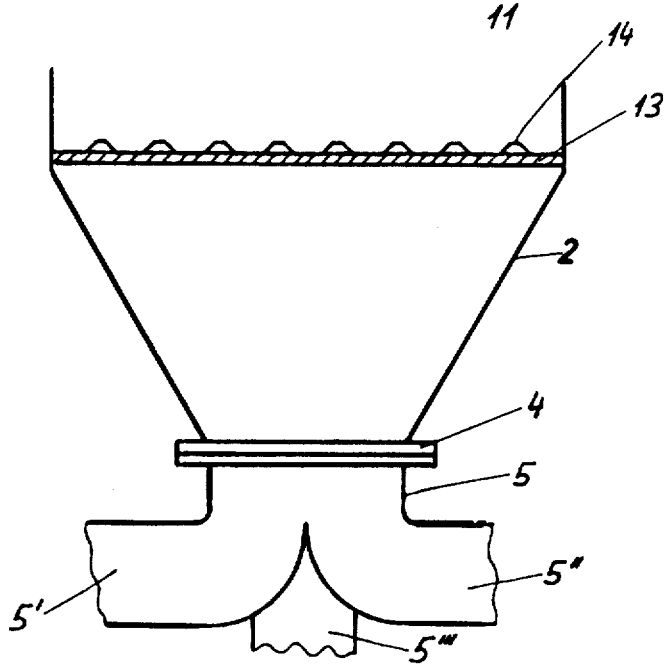
FIG. 2 is the enlarged lower section of the fermentation container showing the apertured bottom wall of the upper section and the substrate introduction conduit to the lower section.

According to FIGS. 1 and 2 the fermentation container is composed of a cylindrical upper container section 1 and a conical lower section 2. The container is provided with a double jacket 3. The lower section is closed by a flange 4, through which a conduit 5 runs, which may be composed of supply pipes 5', 5", 5'''. At cover 6 of the container a mechanical foam separator 7 with an electrical motor 8 can be attached. A gas discharge pipe 9 leads above a sterile air filter (not shown) and can be connected to a vacuum pump (also not shown). One or more conduits 10 are connected with one or more pumps 11, which are fed from a supply conduit 12 above. The conduit 12 branches out into several levels of the container through conduits 12', 12", 12'''. Between the conical and the cylindrical sections of the container an apertured bottom is attached in known manner. The openings 14 in the apertured bottom 13 can be shaped differently, in general, however, they are circular or rectangular.

Figure 3:
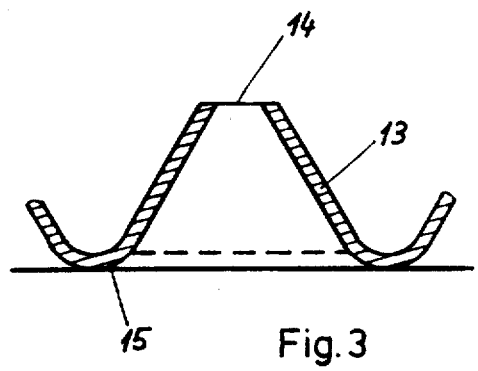
FIGS. 3-7 are different configurations for the openings in the apertured bottom wall.

In FIG. 3 apertured bottom 13 is shaped so that the openings form funnels. They contain round openings 14. The edges 15 are rounded off.

Figure 4:
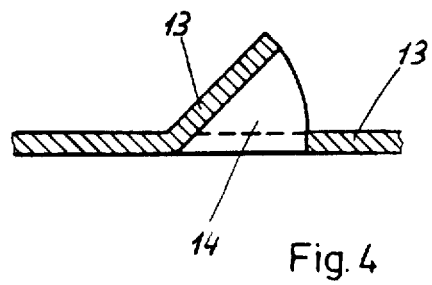

In FIG. 4 the opening 14 is so formed in apertured bottom 13 that a section is bent out. Thereby an oblong, or even a round opening can be formed.

Figure 5:
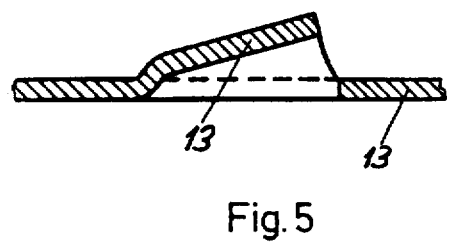
Figure 6:
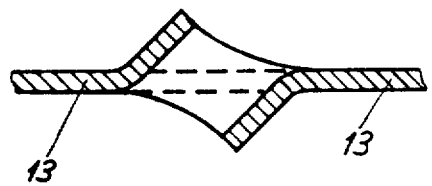

FIGS. 5 and 6 exhibit variations.

Figure 7:
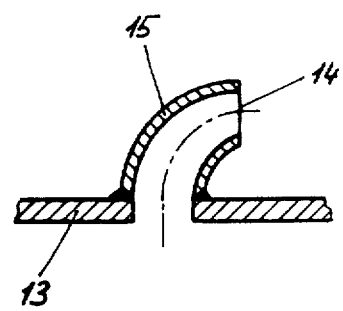

In FIG. 7 the opening 14 is formed through a curved tube or elbow 15, which is able to alter the direction of flow.

Figure 8:
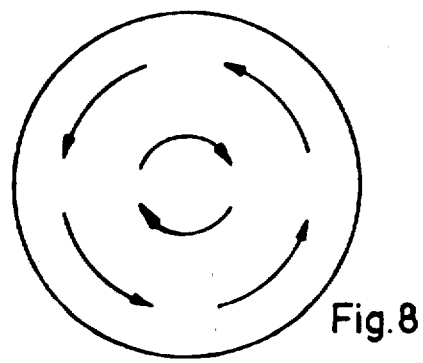
FIG. 8 is a schematic of the direction of movement of the substrate in the upper section after passing through the elbow-shaped openings indicated in FIG. 7.

FIG. 8 reproduces the direction of flow from curved tubes 15.

During operation the substrate together with the microorganisms will be introduced from the upper sections of container 1 at various levels, withdrawn through conduits 12', 12" or 12''' and introduced to conduit piece 12, then through one or more pumps 11. Pumps 11 push the substrate in sufficient quantity, which can be increased by having several parallel-connected pumps. The substrate liquid is pushed across the delivery pipe 5 or 5', 5", 5''' back into the container, i.e., into cone 2. The amount of liquid must be selected so large that a fluid velocity through the opening of flange 4 of about 1.7 meters per second prevails; however, this cannot be more than 2 meters per second. Under these conditions the substrate will be squeezed with higher velocity through the openings 14, along with a decrease in the velocity at the bottom of the openings, which, however, does not result in a settling of the microorganisms.

FIG. 8 indicates the flow scheme whereby elbows 15 of FIG. 7 at the periphery and in the center point in opposite directions as shown by the arrows.

Table I indicates data for the formation of the apertured bottom wall in a 300-cubic-meter-capacity fermentor, which displays a bottom wall 13 diameter of 5800 mm.

TABLE I

| Diameter of openings (mm): | 2.5 | 5 | 7.5 | 10 | 12.5 | 15 |
|---|---|---|---|---|---|---|
| number of openings: | 10,018 | 2,505 | 1,111 | 625 | 400 | 278 |

Table II indicates the dependency of the entrance velocity through the entry connection 4 having a diameter of 5,800 mm. The veloc<sub>i</sub>y through the openings 14 come to about a constant 2 meters per second.

TABLE II

| Velocity in connection 4: | 0.00315 m/s | 0.00631 m/s | 0.00946 m/s |
|---|---|---|---|
| Pumping capacity: | 300 m³/h | 600 m³/h | 900 m³/h |

With the choice of the number and the size of the openings, it turns out to be particularly advantageous if the sum of all of the hole areas in the bottom wall 13 is the same as the area of the cross-section present in the main entry connection 4. This will result in a flow volume in the connection which is about equally as large as the flow volume through the openings of the apertured bottom wall.

At the surface of the substrate material, the gas formed by the anaerobic metabolism separates off, so that indeed accordingly the turbulence produced forms foam. The foam will be separated into its liquid and gaseous components by the mechanical foam separator 7, driven by means of electrical motor 8. Liquid will be separated by the centrifugal force and run back into the container. The gas leaves the container through connector 9, usually through an air filter, which during the heat sterilization of the container with equalization of pressure prevents contaminated air from being able to enter the container.

A particularly advantageous method according to the invention results then through means of external pumps which produce a revolution of substrate and turbulence, without extra loss of heat, so that the fermentation time can be drastically reduced.

It will be understood that each of the elements described above, or two or more together, may also find a useful application in other types of mixing systems differing from the types described above.

While the invention has been illustrated and described as embodied in a fermentor for anaerobic fermentation, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of submerged anerobic fermentation of substrates with microorganisms, comprising the steps of introducing microorganisms and a substrate for the microorganisms into a lower conical section and an apertured bottom wall containing a plurality of openings arranged between the lower conical section and the upper cylindrical section; causing the microorganisms to undergo submerged anaerobic fermentation in the substrate; preventing settling of microorganisms in the container during fermentation by recirculating the substrate and microorganisms by withdrawing the fermenting substrate with microorganisms therein from an outlet opening in the upper cylindrical section, and supplying the withdrawn substrate with microorganisms therein into the lower conical section through an inlet opening below said bottom wall at sufficient velocity and quantity to drive the substrate and microorganisms upward in the fermentation container and up through the openings in the apertured bottom wall at sufficient fluid velocity to prevent settling of the microorganisms in the fermentation container, and said substrate and microorganisms being agitated solely by said recirculating through said openings in the apertured bottom wall.

2. Method according to claim 1, wherein the withdrawing step includes withdrawing the substrate from different levels in the upper cylindrical container section.

3. Method according to claim 1, wherein the openings in the apertured bottom wall one arranged so that the direction of flow above the apertured bottom wall at the periphery of the container is opposite the direction of flow in the center of the container above the apertured bottom wall.

4. Method according to claim 1, wherein the anaerobic microorganisms produce a gas during the fermentation.

5. A method of submerged anaerobic fermentation of substrates with microorganisms, comprising the steps of introducing microorganisms and a substrate for the microorganisms into a fermentation container having an upper cylindrical section, a lower conical section and an apertured bottom wall containing a plurality of openings arranged between the lower conical section and the upper cylindrical section; causing the microorganisms to undergo submerged anaerobic fermentation in the substrate; preventing settling of microorganisms in the container during fermentation by recirculating the substrate and microorganisms by withdrawing the fermenting substrate with microorganisms therein from an outlet opening in the upper cylindrical section, and supplying the withdrawn substrate with microorganisms therein into the lower conical section through an inlet opening below said bottom wall at sufficient velocity and quantity to drive the substrate and microorganisms upward in the fermentation container and up through the openings in the apertured bottom wall at sufficient fluid velocity to prevent settling of the microorganisms in the fermentation container, said plurality of openings in the bottom wall having a total opening area equal to the cross-sectional area of said inlet opening in the lower conical section and said substrate and microorganisms being agitated solely by said recirculating through said openings in the apertured bottom wall.

6. An apparatus for submerged anaerobic fermentation of substrates with microorganisms, consisting essentially of a fermentation container for containing a substrate and microorganisms having an upper cylindrical section, a lower conical section, an apertured bottom wall containing a plurality of openings arranged between the lower conical section and the upper cylindrical section, a means for withdrawing substrate and microorganisms from the upper cylindrical section through an outlet opening therein, and means for supplying the withdrawn substrate and microorganisms at sufficient velocity and quantity into the lower conical section through an inlet opening therein below the bottom wall to drive the substrate and microorganisms upward in the container and up through the openings in the apertured bottom wall at sufficient fluid velocity to prevent settling of the microorganisms in the fermentation container, said apertured bottom wall being the sole means contained by said apparatus for agitation of substrate and microorganisms in said fermentation container.

7. Apparatus according to claim 6, wherein the supplying means includes one or more tubes connected to the inlet opening of the lower conical section.

8. Apparatus according to claim 6, wherein the openings of the apertured bottom wall are cone-shaped.

9. Apparatus according to claim 6, wherein the openings of the apertured bottom wall are circular- or rectangular-shaped.

10. Apparatus according to claim 6, wherein the openings of the apertured bottom wall are formed into curved tubes or elbows.

11. Apparatus according to claim 7, wherein the sum of all the hole areas of the openings of the apertured bottom wall is equal to the size of the cross-sectional area of the tubes connected to the inlet opening of the lower conical section.

12. An apparatus for submerged anaerobic fermentation of substrates with microorganisms, consisting essentially of a fermentation container for containing a substrate and microorganisms having an upper cylindrical section, a lower conical section, an apertured bottom wall containing a plurality of openings arranged between the lower conical section and the upper cylindrical section, a means for withdrawing substrate and microorganisms from the upper cylindrical section through an outlet opening therein, and means for supplying the withdrawn substrate and microorganisms at sufficient velocity and quantity into the lower conical section through an inlet opening therein below the bottom wall to drive the substrate and microorganisms upward in the container and up through the openings in the apertured bottom wall at sufficient fluid velocity to prevent settling of the microorganisms in the fermentation container, said plurality of openings in the apertured bottom wall having a total opening area equal to the cross-sectional area of said inlet opening in the lower conical section.

* * * * *